United States Patent [19]
Iwakura et al.

[11] Patent Number: 6,147,265
[45] Date of Patent: Nov. 14, 2000

[54] PROCESS FOR PRODUCING ALKYLENE GLYCOL

[75] Inventors: Tomoatsu Iwakura; Hidekazu Miyagi, both of Mie, Japan

[73] Assignee: Mitsubishi Chemical Corporation, Tokyo, Japan

[21] Appl. No.: 09/066,773

[22] Filed: Apr. 27, 1998

[30] Foreign Application Priority Data

Apr. 30, 1997 [JP] Japan .................................. 9-112098

[51] Int. Cl.$^7$ .................................................. C07C 27/00
[52] U.S. Cl. ........................................... 568/867; 568/867
[58] Field of Search ............................................. 568/867

[56] References Cited

U.S. PATENT DOCUMENTS

| | | | |
|---|---|---|---|
| 4,393,254 | 7/1983 | Johnson, Jr. et al. | 568/867 |
| 4,560,813 | 12/1985 | Collier | 568/872 |
| 4,937,393 | 6/1990 | Masuda et al. | 568/867 |

FOREIGN PATENT DOCUMENTS

| | | |
|---|---|---|
| 741683 | 8/1997 | European Pat. Off. . |
| 57-139026 | 8/1982 | Japan . |
| 60-56141 | 12/1985 | Japan . |
| 61-501630 | 8/1986 | Japan . |
| 5-47528 | 7/1993 | Japan . |
| 7-289912 | 11/1995 | Japan . |
| 9-215927 | 8/1997 | Japan . |
| 9-508136 | 8/1997 | Japan . |
| WO 95/20559 | 8/1995 | WIPO . |

*Primary Examiner*—James O. Wilson
*Attorney, Agent, or Firm*—Oblon, Spivak, McClelland, Maier & Neustadt, P.C.

[57] ABSTRACT

A process for producing an alkylene glycol which comprises a step of reacting an alkylene oxide with water in the presence of a catalyst, wherein the catalyst comprises an anion-exchange resin comprising: a polymer of a vinylaromatic compound as a substrate; and quaternary ammoniums group each bonded to the respective aromatic groups of the polymer substrate via a connecting group having a chain length of three or more atoms.

12 Claims, No Drawings

PROCESS FOR PRODUCING ALKYLENE GLYCOL

FIELD OF THE INVENTION

The present invention relates to a process for producing an alkylene glycol from an alkylene oxide. Alkylene glycols, especially ethylene glycol, are used as starting materials for resins and used in nonfreezing solutions, etc., and thus are industrially important compounds.

BACKGROUND OF THE INVENTION

The technique of hydrating alkylene oxides to produce alkylene glycols is known. In particular, the production of ethylene glycol by the hydration of ethylene oxide is being conducted at a large scale. However, in conventional techniques, undesirable by-products such as dialkylene glycols and trialkylene glycols are produced besides alkylene glycols. In order to inhibit the generation of such by-products to thereby heighten selectivity for alkylene glycols, water should be used in an amount as large as from 10 to 20 times that of the alkylene oxides. Use of such a large amount of water is undesirable from the standpoint of water removal at a purification step. Use of various catalysts for improving selectivity has been investigated as a means for eliminating the above problem, and many reports have been made thereon.

Although it is known to use an acid or base alone as a catalyst, this technique is insufficient in selectivity improvement.

JP-A-51-127010 discloses the use of a combination of an organic base and carbon dioxide as a catalyst. (The term "JP-A" as used herein means an "unexamined published Japanese patent application".) As the organic base is used a tertiary amine.

JP-B-49-24448 discloses the use of a combination of an alkali halide or ammonium halide and carbon dioxide as a catalyst. (The term "JP-B" as used herein means an "examined Japanese patent publication".)

JP-B-60-45610 discloses the use of a molybdic acid salt as a catalyst.

JP-B-60-45611 discloses the use of a tungstic acid salt as a catalyst.

However, these conventional catalysts have a drawback that they dissolve in the reaction mixture and are hence difficult to recover therefrom. Several reports have hence been made on a technique for fixing the active ingredients of such conventional catalysts.

JP-B-60-56141 discloses the use of a combination of an anion-exchange resin which has undergone exchange for halogen anions and carbon dioxide as a catalyst.

JP-B-5-47528 discloses the use of a solid support, as a catalyst, which has an anion-exchanging ability and has undergone exchange for metal oxide anions such as molybdate ions, tungstate ions or vanadate ions. As the solid support is used an anion-exchange resin.

EP-A-741,683 discloses the use of a solid, as a catalyst, which has an anion-exchanging ability and has undergone exchange for hydrogencarbonate ions, hydrogensulfite ions, carboxylate ions or the like. As the solid is used an anion-exchange resin.

However, anion-exchange resins generally have low heat resistance, and the conventional catalysts each based on an anion-exchange resin do not necessarily have a sufficient catalytic life.

SUMMARY OF THE INVENTION

Accordingly, an object of the present invention is to provide a catalyst which has a prolonged catalytic life and is capable of yielding an alkylene glycol with a high selectivity.

Other objects and effects of the present invention will become apparent from the following description.

The above objectives of the present invention have been achieved by providing:

a process for producing an alkylene glycol which comprises a step of reacting an alkylene oxide with water in the presence of a catalyst, wherein the catalyst comprises an anion-exchange resin comprising:
  a polymer of a vinylaromatic compound as a substrate; and
  quaternary ammonium groups each bonded to the respective aromatic groups of the polymer substrate via a connecting group having a chain length of three or more atoms.

By the use of the above catalyst, the production of alkylene glycol can be conducted with high selectivity over a long period of time.

DETAILED DESCRIPTION OF THE INVENTION

The present invention is described in detail below.

In the present invention, an anion-exchange resin having a structure comprising a polymer of a vinylaromatic compound as a substrate and a quaternary ammonium group bonded to each of aromatic groups of the polymer via a connecting group having a chain length of three or more atoms is used as a catalyst.

The substrate basically has the structure of a polymer of a monovinylaromatic compound, e.g., styrene, vinyltoluene, ethylvinylbenzene or vinylnaphthalene. It preferably has the structure of a crosslinked copolymer formed from such a monovinyl compound and a small proportion of a polyvinyl compound used as a crosslinking agent, e.g., divinylbenzene, divinyltoluene, divinylnaphthalene or ethylene glycol dimethacrylate. In particular, the structure of a crosslinked copolymer formed from styrene and a small proportion of divinylbenzene is preferred.

The connecting group which bonds a quaternary ammonium group to the substrate should have a chain length of three or more atoms. The skeleton of the connecting group generally composed of carbon atoms or a combination of a carbon atom and an oxygen atom.

The anion-exchange resin having such a structure can be produced by copolymerizing a monovinylaromatic compound such as those enumerated above, which is represented by the following general formula (III), with a monovinylaromatic compound having a substituent which contains at the terminal thereof an labile member, such as a halogen atom (e.g., chlorine, bromine or iodine) or a tosyl group, and with a polyvinyl compound such as those enumerated above, and then reacting the resultant copolymer with a tertiary amine.

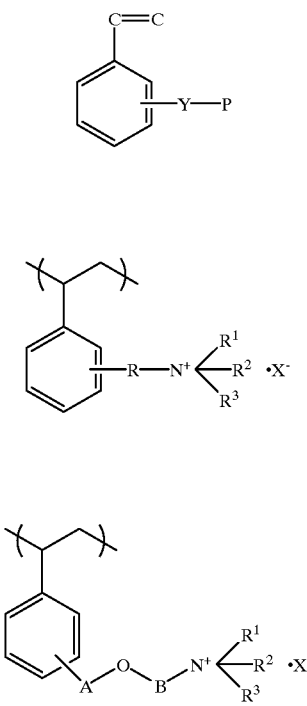

(III)

(I)

(II)

Conversion of propylene oxide (%)={(the number of moles of propylene oxide consumed)/(the number of moles of propylene oxide fed)}×100

Selectivity for propylene glycol (%)={(the number of moles of propylene glycol yielded)/(the number of moles of propylene oxide consumed)}×100

Selectivity for dipropylene glycol (%)={(the number of moles of dipropylene glycol yielded)/(the number of moles of propylene oxide consumed)}×200

Selectivity for tripropylene alycol (%)={(the number of moles of tripropylene glycol yielded)/(the number of moles of propylene oxide consumed)}×300

Conversion of ethylene oxide (%)={(the number of moles of ethylene oxide consumed)/(the number of moles of ethylene oxide fed)}×100

Selectivity for ethylene glycol (%)={(the number of moles of ethylene glycol yielded)/(the number of moles of ethylene oxide consumed)}×100

Selectivity for diethylene glycol (%)={(the number of moles of diethylene glycol yielded)/(the number of moles of ethylene oxide consumed)}×200

Selectivity for triethylene glycol (%)={(the number of moles of triethylene glycol yielded)/(the number of moles of ethylene oxide consumed)}×300

The following anion-exchange resins were used as catalysts.

Catalyst A:

An anion-exchange resin having a structural unit represented by the following formula (IV) (exchange capacity in Cl form, 1.27 meq/ml; water content, 45.7%) produced by suspension-polymerizing styrene having a 4-bromobutyl group with divinylbenzene in an aqueous medium to obtain a crosslinked copolymer, reacting the thus obtained copolymer with trimethylamine to obtain an anion-exchange resin in quaternary ammonium form, and then treating the resin with an aqueous sodium hydrogencarbonate solution to convert the same to the hydrogencarbonate form.

(IV)

Catalyst B:

An anion-exchange resin having a structural unit represented by the following formula (V) (exchange capacity in Cl form, 1.10 meq/ml; water content, 52.7%) produced by suspension-polymerizing styrene having a 3-bromopropyl group with divinylbenzene in an aqueous medium to obtain a crosslinked copolymer and subjecting the thus obtained copolymer to the same treatments as in the production of Catalyst A.

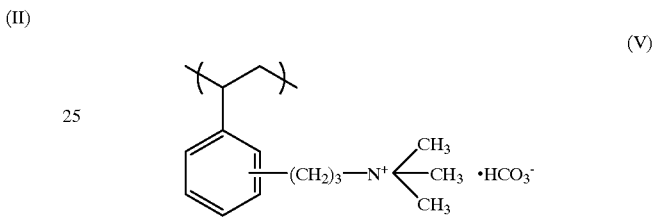

(V)

Catalyst C:

An anion-exchange resin having a structural unit represented by the following formula (VI) (exchange capacity in Cl form, 1.21 meq/ml; water content, 46.6%) produced by suspension-polymerizing styrene having a 4-bromobutoxymethyl group with divinylbenzene in an aqueous medium to obtain a crosslinked copolymer and subjecting the thus obtained copolymer to the same treatments as in the production of Catalyst A.

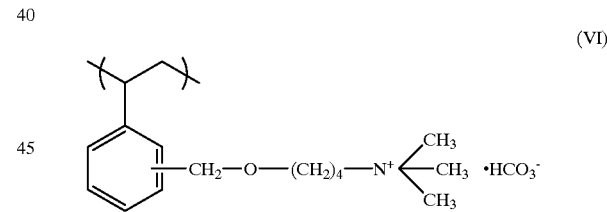

(VI)

Catalyst D:

An anion-exchange resin produced by subjecting DIAION SA10A to ion exchange with an aqueous sodium hydrogencarbonate solution. (The DIAION, a trademark of Mitsubishi Chemical Corp., is manufactured by Mitsubishi Chemical Corp., which has a structure composed of a styrene/divinylbenzene copolymer skeleton and trimethylaminomethyl groups bonded thereto, and has an exchange capacity in Cl form of 1.26 meq/ml and a water content of 45%.)

Catalyst E:

An anion-exchange resin produced by subjecting LEWATIT M511WS to ion exchange with an aqueous sodium hydrogencarbonate solution. (The LEWATIT is manufactured by Bayer Ltd., which has an exchange capacity of 1.4 eq/liter and a water content of from 43 to 49%.)

Catalyst F:

An anion-exchange resin having a structural unit represented by the following formula (VII) produced by subjecting the anion-exchange resin obtained in the course of the production of Catalyst A to ion exchange with an aqueous sodium molybdate solution.

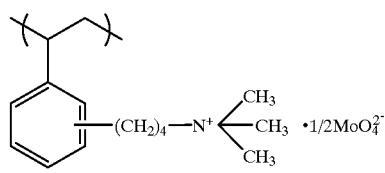

Catalyst G:

An anion-exchange resin having structural units represented by the following formula (VIII) produced by subjecting the anion-exchange resin obtained in the course of the production of Catalyst B to ion exchange with an aqueous sodium molybdate solution.

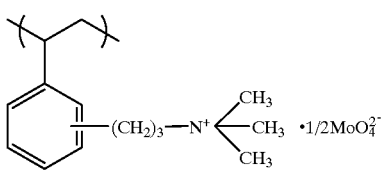

Catalyst H:

An anion-exchange resin having structural units represented by the following formula (IX) produced by subjecting the anion-exchange resin obtained in the course of the production of Catalyst C to ion exchange with an aqueous sodium molybdate solution.

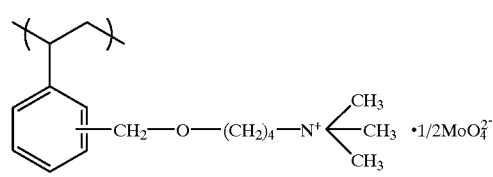

Catalyst I:

An anion-exchange resin produced by subjecting DIAION SA10A to ion exchange with an aqueous sodium molybdate solution.

Catalyst J:

An anion-exchange resin produced by subjecting DOWEX MSA-1 to ion exchange with an aqueous sodium molybdate solution. (The DOWEX is manufactured by Dow Chemical Limited, which has an exchange capacity of 1.2 eq/liter and a water content of from 57 to 63%.)

EXAMPLE 1

Into an SUS autoclave having a capacity of 30 ml were introduced 2 g of the respective catalyst in a wet state, 5.4 g of water, and 8.7 g of propylene oxide. The autoclave was immersed in a 150° C. oil bath to react the reactants for 1.5 hours with stirring. The reaction temperature was 140° C. The resultant reaction mixture was analyzed by gas chromatography. The results obtained are shown in Table 1.

TABLE 1

| Catalyst | A | B | C | D | E | F | G | H | I | J |
|---|---|---|---|---|---|---|---|---|---|---|
| Conversion of propylene oxide (%) | 100 | 100 | 100 | 100 | 100 | 99.3 | 99.7 | 99.8 | 99.6 | 99.8 |
| Selectivity for propylene glycol (%) | 89.0 | 89.0 | 89.4 | 87.3 | 87.6 | 87.2 | 86.7 | 87.0 | 88.6 | 86.1 |
| Selectivity for dipropylene glycol (%) | 10.3 | 10.3 | 9.9 | 11.7 | 11.8 | 11.3 | 11.5 | 11.6 | 10.6 | 13.0 |
| Selectivity for tripropylene glycol (%) | 0.7 | 0.7 | 0.7 | 1.0 | 0.6 | 1.5 | 1.8 | 1.4 | 0.9 | 0.9 |

EXAMPLE 2

Some of the catalysts used in Example 1 were washed with water and then used to carry out the same reaction as in Example 1 under the same conditions. This procedure was repeatedly conducted three times in total (the catalysts were washed each time before use). The results of the third reaction are shown in Table 2.

TABLE 2

| Catalyst | A | B | C | D | E |
|---|---|---|---|---|---|
| Conversion of propylene oxide (%) | 100 | 100 | 100 | 100 | 99.9 |
| Selectivity for propylene glycol (%) | 88.8 | 88.4 | 89.1 | 83.8 | 82.9 |
| Selectivity for dipropylene glycol (%) | 10.5 | 11.1 | 10.3 | 15.5 | 16.4 |
| Selectivity for tripropylene glycol (%) | 0.7 | 0.4 | 0.6 | 1.2 | 0.7 |

EXAMPLE 3

Into an SUS autoclave having a capacity of 30 ml were introduced 2 g of a catalyst in a wet state, 5.4 g of water, and 8.7 g of propylene oxide. The autoclave was immersed in a 150° C. oil bath to react the reactants for 1.5 hours with stirring. Thereafter, the autoclave was kept being immersed in the 150° C. oil bath for 48 hours.

The catalyst was separated from the reaction mixture, washed with water, and then used to conduct the same reaction as in Example 1 under the same conditions. The results obtained are shown in Table 3.

TABLE 3

| Catalyst | A | B | C | D | E | F | G | H | I | J |
|---|---|---|---|---|---|---|---|---|---|---|
| Conversion of propylene oxide (%) | 100 | 100 | 100 | 100 | 100 | 99.3 | 99.7 | 99.8 | 99.6 | 99.8 |
| Selectivity for propylene glycol (%) | 87.1 | 87.3 | 88.0 | 62.8 | 55.1 | 89.1 | 88.7 | 89.4 | 80.7 | 79.7 |
| Selectivity for dipropylene glycol (%) | 12.4 | 12.1 | 11.8 | 33.1 | 37.2 | 10.3 | 10.2 | 9.7 | 17.6 | 18.0 |
| Selectivity for tripropylene glycol (%) | 0.5 | 0.6 | 0.2 | 4.2 | 0.6 | 0.7 | 1.1 | 0.9 | 1.7 | 2.3 |

EXAMPLE 4

Into an SUS autoclave having a capacity of 1500 ml were introduced 40 ml of the respective catalyst in a wet state, 270 g of water and 132 g of ethylene oxide. Catalyst A and D were respectively used as the catalyst. The autoclave was heated so as to maintain the reaction temperature at 120° C. and the reactants were reacted for 2 hours with stirring. The resultant reaction mixture was analyzed by gas chromatography. The results obtained are shown in Table 4.

TABLE 4

| Catalyst | A | D |
|---|---|---|
| Conversion of ethylene oxide (%) | 100 | 100 |
| Selectivity for ethylene glycol (%) | 87.3 | 87.0 |
| Selectivity for diethylene glycol (%) | 12.0 | 12.3 |
| Selectivity for triethylene glycol (%) | 0.6 | 0.7 |

As is apparent from the foregoing results, the anion-exchange resin for use in the present invention, which comprises a substrate and quaternary ammonium groups each bonded thereto via a connecting group having a chain length of three or more atoms, yields an alkylene glycol with a high selectivity even after exposed to a high temperature over a long period of time.

While the invention has been described in detail and with reference to specific examples thereof, it will be apparent to one skilled in the art that various changes and modifications can be made therein without departing from the spirit and scope thereof.

What is claimed is:

1. A process for producing an alkylene glycol which comprises a step of reacting an alkylene oxide with water in the presence of a catalyst, wherein said catalyst comprises an anion-exchange resin comprising:
a polymer of a vinylaromatic compound as a substrate; and
quaternary ammonium groups each bonded to the respective aromatic groups of said polymer substrate via a connecting group having a chain length of three or more atoms.

2. The process according to claim 1, wherein said anion-exchange resin has a structural unit represented by the following formula (I):

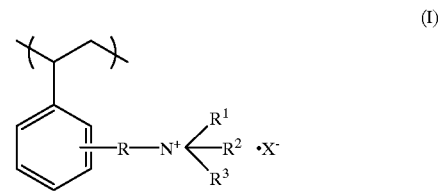

wherein R represents an alkylene group having 3 to 10 carbon atoms, wherein said alkylene group optionally contains a cyclic hydrocarbon group, wherein said group is optionally substituted with an alkyl group; $R^1$, $R^2$ and $R^3$ each represents an alkyl or alkanol group having from 1 to 4 carbon atoms; and $X^-$ represents an anion, and wherein the the benzene ring in formula (I) is optionally substituted with one or more substituents selected from the group consisting of alkyl groups and halogen atoms and is optionally a condensed aromatic ring.

3. The process according to claim 1, wherein said anion-exchange resin has a structural unit represented by the following formula (II):

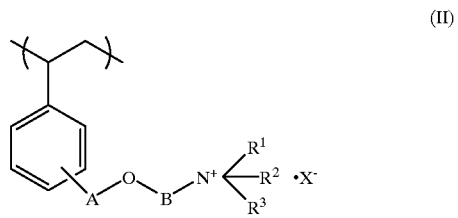

wherein A represents an alkylene group having from 1 to 4 carbon atoms, wherein said group is optionally substituted with an alkyl group, B represents an alkylene group having from 1 to 8 carbon atoms which is optionally substituted with an alkyl group; $R^1$, $R^2$ and $R^3$ each represents an alkyl or alkanol group having from 1 to 4 carbon atoms; and $X^-$ represents an anion, and wherein the the benzene ring in formula (II) is optionally substituted with one or more substituents selected from the group consisting of alkyl groups and halogen atoms and is optionally a condensed aromatic ring.

4. The process according to claim 1, wherein said polymer substrate of the anion-exchange resin is a crosslinked copolymer of vinylaromatic compounds.

5. The process according to claim 4, wherein said polymer substrate is a crosslinked copolymer of styrene and divinylbenzene.

6. The process according to claim 1, wherein said alkylene oxide is ethylene oxide or propylene oxide.

7. The process according to claim 2, wherein said anion is a hydroxyl ion, a chlorine ion, a bromine ion, an iodine ion, a molybdate ion, a tungstate ion, a metavanadate ion, a pyrovanadate ion, a hydrogenpyrovanadate ion, a hydrogensulfite ion, a carboxylate ion or a hydrogencarbonate ion.

8. The process according to claim 7, wherein said anion is a molybdate ion, a tungstate ion, a metavanadate ion, a pyrovanadate ion, a hydrogenpyrovanadate ion, a carboxylate ion or a hydrogencarbonate ion.

9. The process according to claim 3, wherein said anion is a hydroxyl ion, a chlorine ion, a bromine ion, an iodine ion, a molybdate ion, a tungstate ion, a metavanadate ion, a pyrovanadate ion, a hydrogenpyrovanadate ion, a hydrogensulfite ion, a carboxylate ion or a hydrogencarbonate ion.

10. The process according to claim 9, wherein said anion is a molybdate ion, a tungstate ion, a metavanadate ion, a pyrovanadate ion, a hydrogenpyrovanadate ion, a carboxylate ion or a hydrogencarbonate ion.

11. The process according to claim 1, wherein the reaction is conducted at a temperature of from 50 to 200° C.

12. The process according to claim 1, wherein the reaction is conducted at a pressure of from 0.1 to 5 MPa.

* * * * *